United States Patent
Sur

(10) Patent No.: US 10,813,385 B2
(45) Date of Patent: Oct. 27, 2020

(54) BUCK REGULATOR WITH OPERATIONAL AMPLIFIER FEEDBACK FOR AN AEROSOL DELIVERY DEVICE

(71) Applicant: RAI STRATEGIC HOLDINGS, INC., Winston-Salem, NC (US)

(72) Inventor: Rajesh Sur, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 228 days.

(21) Appl. No.: 15/916,696

(22) Filed: Mar. 9, 2018

(65) Prior Publication Data

US 2019/0274353 A1 Sep. 12, 2019

(51) Int. Cl.
*A24F 13/00* (2006.01)
*A24F 17/00* (2006.01)
(Continued)

(52) U.S. Cl.
CPC .......... *A24F 47/008* (2013.01); *A24B 15/167* (2016.11); *A61M 11/042* (2014.02); *A61M 15/06* (2013.01); *A61M 2016/0024* (2013.01); *A61M 2016/0027* (2013.01); *A61M 2016/0039* (2013.01); *A61M 2205/3317* (2013.01); *A61M 2205/3653* (2013.01); *A61M 2205/50* (2013.01);
(Continued)

(58) Field of Classification Search
CPC .................................................... A24F 47/008
USPC ....................................................... 131/329
See application file for complete search history.

(56) References Cited

U.S. PATENT DOCUMENTS 2,057,353 A 10/1936 Whittemore, Jr.
2,104,266 A 1/1938 McCormick
(Continued)

FOREIGN PATENT DOCUMENTS

CN 1541577 11/2004
CN 2719043 8/2005
(Continued)

OTHER PUBLICATIONS

Deng, "A primer on high-side FET load switches (Part 1 of 2)", EE Times, May 2007, retrieved Oct. 2017, 5 pgs.
(Continued)

*Primary Examiner* — Abdullah A Riyami
*Assistant Examiner* — Thang H Nguyen
(74) *Attorney, Agent, or Firm* — Womble Dickinson (US) LLP

(57) ABSTRACT

An aerosol delivery device is provided that includes a heating element configured to convert electricity to heat and thereby vaporize components of an aerosol precursor composition, and a control component coupled to and configured to controllably power the heating element. The control component includes a buck regulator circuit coupled to the heating element, and an operational amplifier circuit coupled to the heating element and buck regulator circuit. The buck regulator circuit is configured to step down voltage and step up current from a power source to the heating element to thereby power the heating element. The operational amplifier circuit is configured to amplify an output voltage from the heating element to produce a higher voltage that is fed back to the buck regulator circuit, which is configured to use the higher voltage to regulate an output voltage from the buck regulator circuit to the heating element.

16 Claims, 9 Drawing Sheets

(51) Int. Cl.
  *A24F 25/00*     (2006.01)
  *A24F 47/00*     (2020.01)
  *A24B 15/167*    (2020.01)
  *A61M 15/06*     (2006.01)
  *A61M 11/04*     (2006.01)
  *A61M 16/00*     (2006.01)
  *H02M 3/156*     (2006.01)

(52) U.S. Cl.
  CPC . *A61M 2205/582* (2013.01); *A61M 2205/583* (2013.01); *A61M 2205/587* (2013.01); *A61M 2205/8206* (2013.01); *H02M 3/156* (2013.01)

(56) References Cited

U.S. PATENT DOCUMENTS

| | | | |
|---|---|---|---|
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |
| 5,261,424 | A | 11/1993 | Sprinkel, Jr. |
| 5,388,574 | A | 2/1995 | Ingebrethsen et al. |
| 5,530,225 | A | 6/1996 | Hajaligol |
| 5,668,465 | A * | 9/1997 | May .............. G01R 19/16542 361/86 |
| 5,687,746 | A | 11/1997 | Rose et al. |
| 5,726,421 | A | 3/1998 | Fleischhauer et al. |
| 5,865,185 | A | 2/1999 | Collins et al. |
| 5,894,841 | A | 4/1999 | Voges |
| 5,999,433 | A * | 12/1999 | Hua .............. H02M 3/337 363/132 |
| 6,125,853 | A | 10/2000 | Susa et al. |
| 6,155,268 | A | 12/2000 | Takeuchi |
| 7,117,867 | B2 | 10/2006 | Cox et al. |
| 7,832,410 | B2 | 11/2010 | Hon |
| 8,314,591 | B2 | 11/2012 | Terry et al. |
| 8,365,742 | B2 | 2/2013 | Hon |
| 8,499,766 | B1 | 8/2013 | Newton |
| 2005/0016550 | A1 | 1/2005 | Katase |
| 2006/0196518 | A1 | 9/2006 | Hon |
| 2008/0092912 | A1 | 4/2008 | Robinson et al. |
| 2009/0095311 | A1 | 4/2009 | Hon |
| 2009/0126745 | A1 | 5/2009 | Hon |
| 2009/0188490 | A1 | 7/2009 | Hon |
| 2009/0272379 | A1 | 11/2009 | Thorens et al. |
| 2011/0094523 | A1 | 4/2011 | Thorens et al. |
| 2011/0126848 | A1 | 6/2011 | Zuber et al. |
| 2011/0155718 | A1 | 6/2011 | Greim et al. |
| 2011/0168194 | A1 | 7/2011 | Hon |
| 2011/0265806 | A1 | 11/2011 | Alarcon et al. |
| 2011/0290248 | A1 | 12/2011 | Schennum |
| 2012/0111347 | A1 | 5/2012 | Hon |
| 2012/0260927 | A1 | 10/2012 | Liu |
| 2012/0279512 | A1 | 11/2012 | Hon |
| 2013/0037041 | A1 | 2/2013 | Worm et al. |
| 2013/0056013 | A1 | 3/2013 | Terry et al. |
| 2013/0306084 | A1 | 11/2013 | Flick |
| 2014/0000638 | A1 | 1/2014 | Sebastian et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0209105 | A1 | 7/2014 | Sears et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0261495 | A1 | 9/2014 | Novak et al. |
| 2014/0270727 | A1 | 9/2014 | Ampolini et al. |
| 2014/0270729 | A1 | 9/2014 | DePiano et al. |
| 2014/0270730 | A1 | 9/2014 | DePiano et al. |
| 2014/0299137 | A1 * | 10/2014 | Kieckbusch .......... A24F 47/008 131/328 |
| 2015/0357839 | A1 * | 12/2015 | Cai ....................... A24F 47/008 131/329 |
| 2017/0070141 | A1 * | 3/2017 | Mahmoudi ............. H02M 1/36 |
| 2017/0112194 | A1 | 4/2017 | Sur et al. |
| 2017/0196263 | A1 | 7/2017 | Sur |
| 2017/0196270 | A1 | 7/2017 | Vick et al. |
| 2019/0265740 | A1 * | 8/2019 | Kyakuno ........... H02M 3/33507 |
| 2019/0364973 | A1 * | 12/2019 | Kaufman ............... H05B 6/105 |

FOREIGN PATENT DOCUMENTS

| | | |
|---|---|---|
| CN | 201379072 | 1/2010 |
| CN | 106339026 A | 1/2017 |
| CN | 206586398 U | 10/2017 |
| EP | 0 295 122 | 12/1988 |
| EP | 0 845 220 | 6/1998 |
| EP | 1 618 803 | 1/2006 |
| GB | 2469850 | 11/2010 |
| WO | 94/06314 A1 | 3/1994 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | 2015/100361 A1 | 7/2015 |

OTHER PUBLICATIONS

"5.5 V, 5 A/6 A, High Efficiency, Step-Down DC-to-DC Regulators with Output Tracking", Analog Devices, 2016, p. 1-23.
"CMOS Rail-to-Rail General-Purpose Amplifiers" Analog Devices, 2011, p. 1-20.
International Search Report from corresponding International Appl. No. PCT/IB2019/051817, dated Jul. 11, 2019.
Schrüfer, Elmar, "Messverstärker," Elektrische Messtechnik, Dec. 31, 1990, Carl Hanser Verlag, München, Wien, pp. 121-140.

* cited by examiner

BUCK REGULATOR WITH OPERATIONAL AMPLIFIER FEEDBACK FOR AN AEROSOL DELIVERY DEVICE

TECHNOLOGICAL FIELD

The present disclosure relates to aerosol delivery devices such as electronic cigarettes and heat-not-burn cigarettes. The aerosol delivery device may be configured to heat an aerosol precursor composition, which may be made or derived from tobacco or otherwise incorporate tobacco, to form an inhalable substance for human consumption.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith, Jr. et al., and U.S. Pat. App. Pub. No. 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference. Other representative cigarettes or smoking articles that have been described and, in some instances, been made commercially available include those described in U.S. Pat. No. 4,735,217 to Gerth et al., U.S. Pat. Nos. 4,922,901, 4,947,874, and 4,947,875 to Brooks et al., U.S. Pat. No. 5,060,671 to Counts et al., U.S. Pat. No. 5,249,586 to Morgan et al., U.S. Pat. No. 5,388,594 to Counts et al., U.S. Pat. No. 5,666,977 to Higgins et al., U.S. Pat. No. 6,053,176 to Adams et al., U.S. Pat. No. 6,164,287 to White, U.S. Pat. No. 6,196,218 to Voges, U.S. Pat. No. 6,810,883 to Felter et al., U.S. Pat. No. 6,854,461 to Nichols, U.S. Pat. No. 7,832,410 to Hon, U.S. Pat. No. 7,513,253 to Kobayashi, U.S. Pat. No. 7,726,320 to Robinson et al., U.S. Pat. No. 7,896,006 to Hamann, U.S. Pat. No. 6,772,756 to Shayan, U.S. Pat. Pub. No. 2009/0095311 to Hon, U.S. Pat. Pub. Nos. 2006/0196518, 2009/0126745, and 2009/0188490 to Hon, U.S. Pat. Pub. No. 2009/0272379 to Thorens et al., U.S. Pat. Pub. Nos. 2009/0260641 and 2009/0260642 to Monsees et al., U.S. Pat. Pub. Nos. 2008/0149118 and 2010/0024834 to Oglesby et al., U.S. Pat. Pub. No. 2010/0307518 to Wang, and PCT Pat. App. Pub. No. WO 2010/091593 to Hon, which are incorporated herein by reference.

Representative products that resemble many of the attributes of traditional types of cigarettes, cigars or pipes have been marketed as ACCORD® by Philip Morris Incorporated, ALPHA™, JOYE 510™ and M4™ by InnoVapor LLC, CIRRUS™ and FLING™ by White Cloud Cigarettes, BLU™ by Fontem Ventures B.V., COHITA™, COLIBRI™, ELITE CLASSIC™, MAGNUM™, PHANTOM™ and SENSE™ by EPUFFER® International Inc., DUOPRO™, STORM™ and VAPORKING® by Electronic Cigarettes, Inc., EGAR™ by Egar Australia, eGo-C™ and eGo-T™ by Joyetech, ELUSION™ by Elusion UK Ltd, EONSMOKE® by Eonsmoke LLC, FIN™ by FIN Branding Group, LLC, SMOKE® by Green Smoke Inc. USA, GREENARETTE™ by Greenarette LLC, HALLIGAN™, HENDU™, JET™, MAXXQ™, PINK™ and PITBULL™ by SMOKE STIK®, HEATBAR™ and IQOS™ by Philip Morris International, Inc., HYDRO IMPERIAL™ and LXE™ from Crown7, LOGIC™ and THE CUBAN™ by LOGIC Technology, LUCI® by Luciano Smokes Inc., METRO® by Nicotek, LLC, NJOY® and ONEJOY™ by Sottera, Inc., NO. 7™ by SS Choice LLC, PREMIUM ELECTRONIC CIGARETTE™ by PremiumEstore LLC, RAPP E-MYSTICK™ by Ruyan America, Inc., RED DRAGON™ by Red Dragon Products, LLC, RUYAN® by Ruyan Group (Holdings) Ltd., SF® by Smoker Friendly International, LLC, GREEN SMART SMOKER® by The Smart Smoking Electronic Cigarette Company Ltd., SMOKE ASSIST® by Coastline Products LLC, SMOKING EVERYWHERE® by Smoking Everywhere, Inc., V2CIGS™ by VMR Products LLC, VAPOR NINE™ by VaporNine LLC, VAPOR4LIFE® by Vapor 4 Life, Inc., VEPPO™ by E-CigaretteDirect, LLC, VUSE® by R. J. Reynolds Vapor Company, Mistic Menthol product by Mistic Ecigs, the Vype product by CN Creative Ltd., and GLO™ by British American Tobacco. Yet other electrically powered aerosol delivery devices, and in particular those devices that have been characterized as so-called electronic cigarettes, have been marketed under the tradenames COOLER VISIONS™, DIRECT E-CIG™ DRAGONFLY™, EMIST™, EVERSMOKE™, GAMUCCI®, HYBRID FLAME™, KNIGHT STICKS™, ROYAL BLUES™, SMOKETIP®, SOUTH BEACH SMOKE™.

However, it may be desirable to provide aerosol delivery devices with improved electronics such as may extend usability of the devices.

BRIEF SUMMARY

The present disclosure relates to aerosol delivery devices configured to produce aerosol and which aerosol delivery devices, in some implementations, may be referred to as electronic cigarettes or heat-not-burn cigarettes. The present disclosure includes, without limitation, the following example implementations.

Some example implementations provide an aerosol delivery device comprising an aerosol delivery device comprising a housing structured to retain an aerosol precursor composition; a heating element configured to convert electricity to heat and thereby vaporize components of the aerosol precursor composition; and a control component coupled to and configured to controllably power the heating element, the control component including: a buck regulator circuit coupled to the heating element, and configured to step down voltage and step up current from a power source to the heating element to thereby power the heating element; and an operational amplifier circuit coupled to the heating element and buck regulator circuit, and configured to amplify an output voltage from the heating element to produce a higher voltage that is fed back to the buck regulator circuit, wherein the buck regulator circuit includes a power stage configured to step down the voltage and step up the current from the power source, and a feedback control circuit configured to use the higher voltage from the operational amplifier circuit to regulate an output voltage from the buck regulator circuit to the heating element.

In some example implementations of the aerosol delivery device of any preceding example implementation, or any combination of any preceding example implementations, the aerosol delivery device further comprises a positive terminal to which the power source is connected or connectable, wherein the control component further includes a high-side load switch between the buck regulator circuit and the positive terminal, the high-side load switch being configured to connect and disconnect the power source to and from a load including the heating element, and limit input current to the buck regulator circuit.

In some example implementations of the aerosol delivery device of any preceding example implementation, or any combination of any preceding example implementations, the aerosol delivery device further comprises a sensor between the positive terminal and the high-side load switch, the sensor being configured to produce a measurement of pressure caused by airflow through at least a portion of the aerosol delivery device, and convert the measurement of pressure to a corresponding electrical signal, and wherein the control component further includes a processor configured to receive the corresponding electrical signal and control the high-side load switch to connect the power source to the load in response thereto.

In some example implementations of the aerosol delivery device of any preceding example implementation, or any combination of any preceding example implementations, the feedback control circuit includes an error amplifier and a pulse width modulation (PWM) comparator, the error amplifier being configured to produce a control voltage based on a comparison of the higher voltage and a reference voltage, and the PWM comparator being configured to use the control voltage to produce a PWM waveform that is used to regulate the output voltage from the buck regulator circuit to the heating element.

In some example implementations of the aerosol delivery device of any preceding example implementation, or any combination of any preceding example implementations, the operational amplifier circuit is a non-inverting operational amplifier circuit.

In some example implementations of the aerosol delivery device of any preceding example implementation, or any combination of any preceding example implementations, the aerosol delivery device further comprises a resistor coupled in series between the operational amplifier circuit and the buck regulator circuit, the resistor being configured to limit current fed back to the buck regulator circuit from the operational amplifier circuit.

In some example implementations of the aerosol delivery device of any preceding example implementation, or any combination of any preceding example implementations, the aerosol precursor composition is a liquid, or a solid or semi-solid.

In some example implementations of the aerosol delivery device of any preceding example implementation, or any combination of any preceding example implementations, the aerosol precursor composition is a first aerosol precursor composition that is a solid or semi-solid, the heating element is a first heating element configured to vaporize components of the first aerosol precursor composition, and the aerosol delivery device further comprises terminals coupled or coupleable to a second heating element of a cartridge configured to retain a second aerosol precursor composition that is a liquid, and the second heating element being configured to convert electricity to heat and thereby vaporize components of the second aerosol precursor composition, and wherein the control component further includes a switch coupled to an output of the buck regulator circuit and switchable to provide an output voltage and current from the buck regulator circuit to the first heating element or the second heating element.

In some example implementations of the aerosol delivery device of any preceding example implementation, or any combination of any preceding example implementations, the switch is switchable to provide the output voltage and current from the buck regulator circuit to the first heating element when the second heating element is not coupled to the terminals, and to the second heating element when the second heating element is coupled to the terminals.

In some example implementations of the aerosol delivery device of any preceding example implementation, or any combination of any preceding example implementations, the control component further includes a processor configured to determine when the second heating element is coupled to the terminals; and one or more logic gates with a first input coupled to the output of the buck regulator circuit between the buck regulator circuit and the switch, a second input coupled to the processor, and an output coupled to the switch, wherein the output voltage from the buck regulator circuit causes a logical high level of voltage at the first input of the one or more logic gates, and wherein the processor is configured to cause a first logical level of voltage at the second input of the one or more logic gates when the second heating element is not coupled to the terminals to cause a logical low level of voltage at the output of the one or more logic gates that is configured to control the switch to provide the output voltage and current to the first heating element, and the processor is configured to cause an opposite, second logical level of voltage at the second input of the one or more logic gates when the second heating element is coupled to the terminals to cause a logical high level of voltage at the output of the one or more logic gates that is configured to control the switch to provide the output voltage and current to the second heating element.

Some example implementations provide a control body for an aerosol delivery device, the control body comprising a heating element or terminals coupleable to the heating element, the heating element being configured to convert electricity to heat and thereby vaporize components of an aerosol precursor composition; and a control component coupled to and configured to controllably power the heating element, the control component including: a buck regulator circuit coupled to the heating element, and configured to step down voltage and step up current from a power source to the heating element to thereby power the heating element; and an operational amplifier circuit coupled to the heating element and buck regulator circuit, and configured to amplify an output voltage from the heating element to produce a higher voltage that is fed back to the buck regulator circuit, wherein the buck regulator circuit includes a power stage configured to step down the voltage and step up the current from the power source, and a feedback control circuit configured to use the higher voltage from the operational amplifier circuit to regulate an output voltage from the buck regulator circuit to the heating element.

In some example implementations of the control body of any preceding example implementation, or any combination of any preceding example implementations, the control body further comprises a positive terminal to which the power source is connected or connectable, wherein the control component further includes a high-side load switch between the buck regulator circuit and the positive terminal, the high-side load switch being configured to connect and disconnect the power source to and from a load including the heating element, and limit input current to the buck regulator circuit.

In some example implementations of the control body of any preceding example implementation, or any combination of any preceding example implementations, the control body further comprises a sensor between the positive terminal and the high-side load switch, the sensor being configured to produce a measurement of pressure caused by airflow through at least a portion of the aerosol delivery device, and convert the measurement of pressure to a corresponding electrical signal, and wherein the control component further includes a processor configured to receive the corresponding electrical signal and control the high-side load switch to connect the power source to the load in response thereto.

In some example implementations of the control body of any preceding example implementation, or any combination of any preceding example implementations, the feedback control circuit includes an error amplifier and a pulse width modulation (PWM) comparator, the error amplifier being configured to produce a control voltage based on a comparison of the higher voltage and a reference voltage, and the PWM comparator being configured to use the control voltage to produce a PWM waveform that is used to regulate the output voltage from the buck regulator circuit to the heating element.

In some example implementations of the control body of any preceding example implementation, or any combination of any preceding example implementations, the operational amplifier circuit is a non-inverting operational amplifier circuit.

In some example implementations of the control body of any preceding example implementation, or any combination of any preceding example implementations, the control body further comprises a resistor coupled in series between the operational amplifier circuit and the buck regulator circuit, the resistor being configured to limit current fed back to the buck regulator circuit from the operational amplifier circuit.

In some example implementations of the control body of any preceding example implementation, or any combination of any preceding example implementations, the aerosol precursor composition is a liquid, or a solid or semi-solid.

In some example implementations of the control body of any preceding example implementation, or any combination of any preceding example implementations, the control body includes the heating element that is a first heating element configured to vaporize components of a first aerosol precursor composition that is a solid or semi-solid, and the terminals coupleable to a second heating element configured to convert electricity to heat and thereby vaporize components of a second aerosol precursor composition that is a liquid, and wherein the control component further includes a switch coupled to an output of the buck regulator circuit and switchable to provide an output voltage and current from the buck regulator circuit to the first heating element or the second heating element.

In some example implementations of the control body of any preceding example implementation, or any combination of any preceding example implementations, the switch is switchable to provide the output voltage and current from the buck regulator circuit to the first heating element when the second heating element is not coupled to the terminals, and to the second heating element when the second heating element is coupled to the terminals.

In some example implementations of the control body of any preceding example implementation, or any combination of any preceding example implementations, the control component further includes a processor configured to determine when the second heating element is coupled to the terminals; and a one or more logic gates with a first input coupled to the output of the buck regulator circuit between the buck regulator circuit and the switch, a second input coupled to the processor, and an output coupled to the switch, wherein the output voltage from the buck regulator circuit causes a logical high level of voltage at the first input of the one or more logic gates, and wherein the processor is configured to cause a first logical level of voltage at the second input of the one or more logic gates when the second heating element is not coupled to the terminals to cause a logical low level of voltage at the output of the one or more logic gates that is configured to control the switch to provide the output voltage and current to the first heating element, and the processor is configured to cause an opposite, second logical level of voltage at the second input of the one or more logic gates when the second heating element is coupled to the terminals to cause a logical high level of voltage at the output of the one or more logic gates that is configured to control the switch to provide the output voltage and current to the second heating element.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

FIG. 1 illustrates a perspective view of an aerosol delivery device including a comprising a cartridge and a control body that are coupled to one another, according to an example implementation of the present disclosure;

Figure 3:
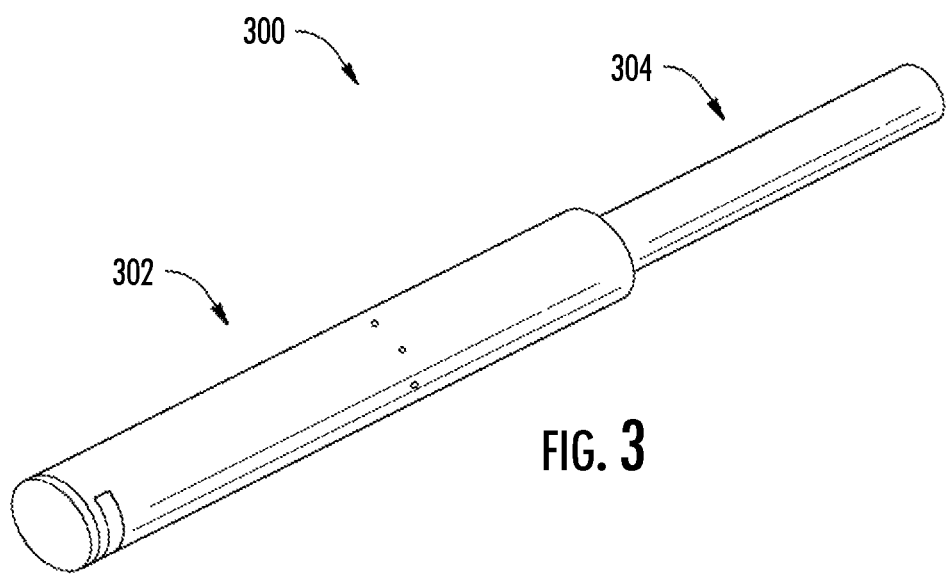
FIGS. 3 and 4 illustrate a perspective view of an aerosol delivery device comprising a control body and an aerosol source member that are respectively coupled to one another and decoupled from one another, according to another example implementation of the present disclosure.
Figure 4:
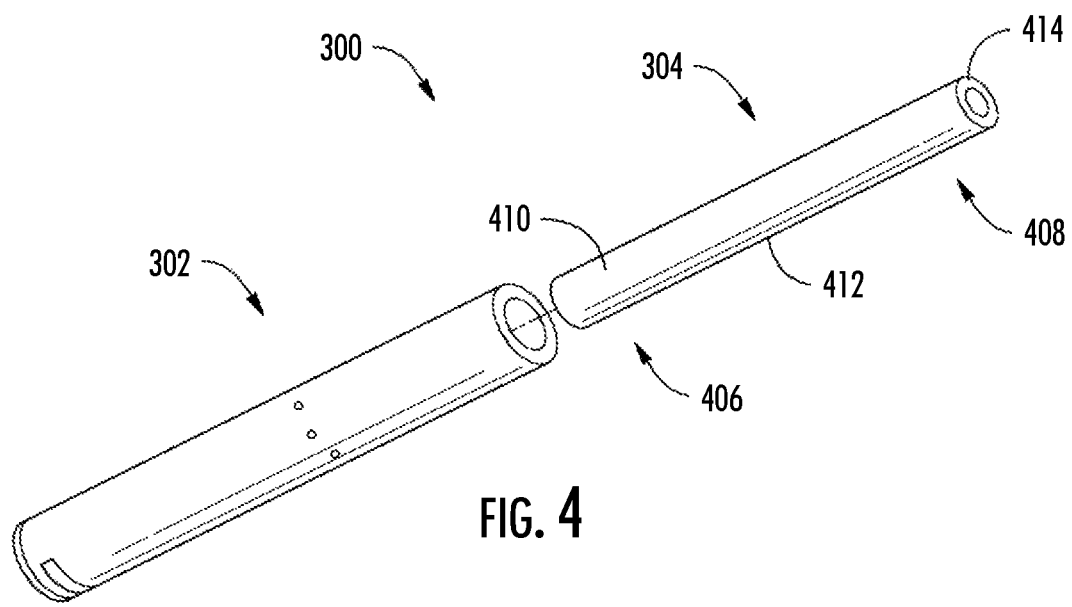
Figure 5:
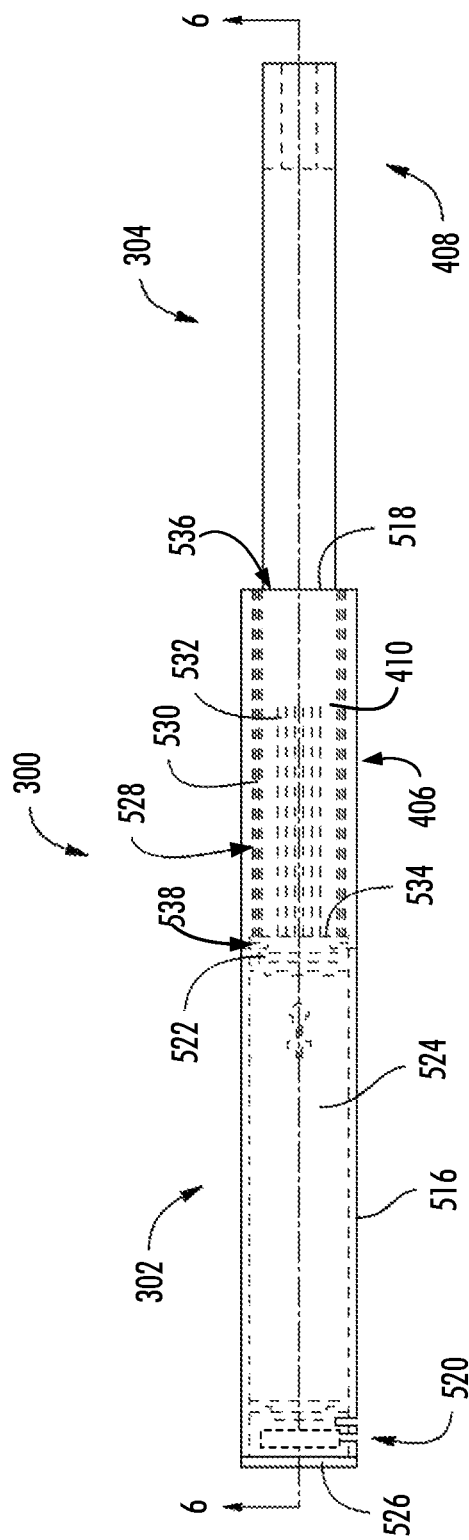
Figure 6:
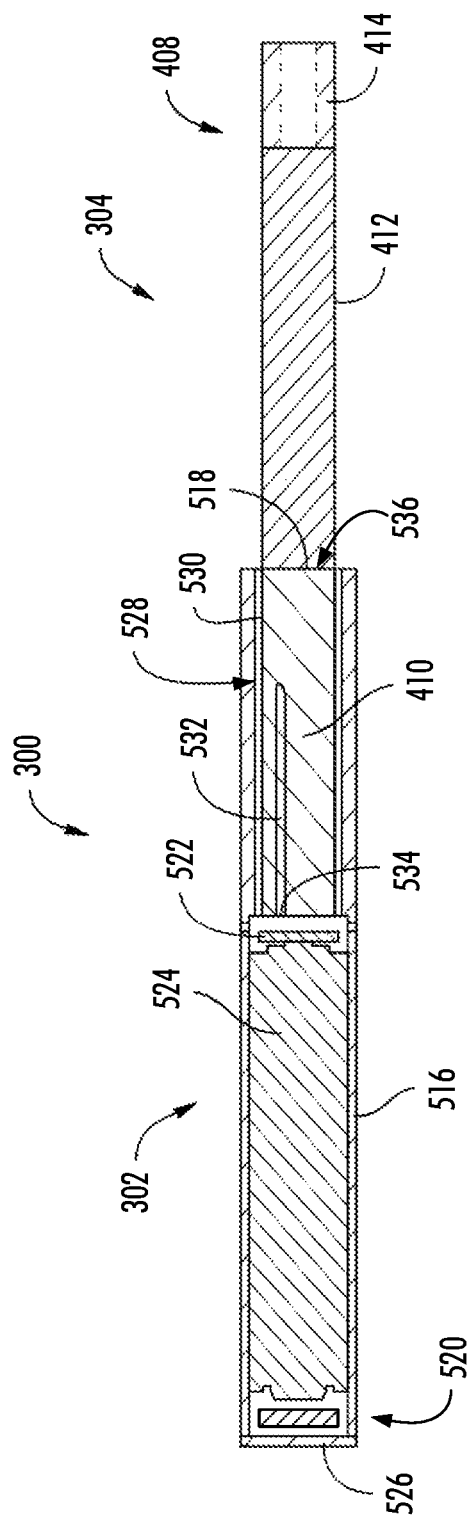

FIGS. 5 and 6 illustrate respectively a front view of and a sectional view through the aerosol delivery device of FIGS. 3 and 4, according to an example implementation; and FIGS. 7A, 7B, 8 and 9 are circuit diagrams of aerosol delivery devices according to various example implementations of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Aerosol delivery devices according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with example implementations of the present disclosure can hold and use that piece much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called "e-cigarettes," "tobacco heating products" and the like (generally referred to as e-cigarettes), it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer housing, which may be referred to as a body or shell. The overall design of the housing can vary, and the format or configuration of the housing that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated housing that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing cartridge). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow from the power source to other components of the aerosol delivery device), a heating element (e.g., an electrical resistance or induction heating element or component(s) commonly referred to as part of an "atomizer"), and an aerosol precursor composition (e.g., a solid tobacco material, a semi-solid tobacco material or a liquid aerosol precursor composition), and a mouth end region or tip for allowing draw upon the aerosol delivery device for aerosol inhalation (e.g., a defined airflow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element may be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other power source to provide current flow sufficient to provide various functionalities to the aerosol delivery device, such as powering of a heating element, powering of control systems, powering of indicators, and the like. The power source can take on various implementations. Preferably, the power source is able to deliver sufficient power to rapidly activate the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

As described hereinafter, the present disclosure relates to aerosol delivery devices. Aerosol delivery devices may be configured to heat an aerosol precursor composition (sometimes referred to as an inhalable substance medium) to produce an aerosol (an inhalable substance). The aerosol precursor composition may comprise one or more of a solid tobacco material, a semi-solid tobacco material, and a liquid aerosol precursor composition. In some implementations, the aerosol delivery devices may be configured to heat and produce an aerosol from a fluid aerosol precursor composition (e.g., a liquid aerosol precursor composition). Such aerosol delivery devices may include so-called electronic cigarettes.

Representative types of liquid aerosol precursor components and formulations are set forth and characterized in U.S. Pat. No. 7,726,320 to Robinson et al., U.S. Pat. No. 9,254,002 to Chong et al., and U.S. Pat. App. Pub. Nos. 2013/0008457 to Zheng et al., 2015/0020823 to Lipowicz et al., and 2015/0020830 to Koller, as well as PCT Pat. App. Pub. No. WO 2014/182736 to Bowen et al., and U.S. Pat. No. 8,881,737 to Collett et al., the disclosures of which are incorporated herein by reference. Other aerosol precursors that may be employed include the aerosol precursors that have been incorporated in any of a number of the representative products identified above. Also desirable are the so-called "smoke juices" for electronic cigarettes that have been available from Johnson Creek Enterprises LLC. Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al., U.S. Pat. No. 5,178,878 to Wehling et al., U.S. Pat. No. 5,223,264 to Wehling et al., U.S. Pat. No. 6,974,590 to Pather et al., U.S. Pat. No. 7,381,667 to Bergquist et al., U.S. Pat. No. 8,424,541 to Crawford et al, U.S. Pat. No. 8,627,828 to Strickland et al., and U.S. Pat. No. 9,307,787 to Sun et al., as well as U.S. Pat. App. Pub. Nos. 2010/0018539 to Brinkley et al., and PCT Pat. App. Pub. No. WO 97/06786 to Johnson et al., all of which are incorporated by reference herein.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

In other implementations, the aerosol delivery devices may comprise heat-not-burn devices, configured to heat a solid aerosol precursor composition (e.g., an extruded tobacco rod) or a semi-solid aerosol precursor composition (e.g., a glycerin-loaded tobacco paste). The aerosol precursor composition may comprise tobacco-containing beads, tobacco shreds, tobacco strips, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or moldable (e.g., extrudable) substrate. Representative types of solid and semi-solid aerosol precursor compositions and formulations are disclosed in U.S. Pat. No. 8,424,538 to Thomas et al., U.S. Pat. No. 8,464,726 to Sebastian et al., U.S. Pat. App. Pub. No. 2015/0083150 to Conner et al., U.S. Pat. App. Pub. No. 2015/0157052 to Ademe et al., and U.S. Pat. App. Pub. No. 2017/0000188 to Nordskog et al., all of which are incorporated by reference herein.

In various implementations, the inhalable substance specifically may be a tobacco component or a tobacco-derived material (i.e., a material that is found naturally in tobacco that may be isolated directly from the tobacco or synthetically prepared). For example, the aerosol precursor composition may comprise tobacco extracts or fractions thereof combined with an inert substrate. The aerosol precursor composition may further comprise unburned tobacco or a composition containing unburned tobacco that, when heated to a temperature below its combustion temperature, releases an inhalable substance. In some implementations, the aerosol precursor composition may comprise tobacco condensates or fractions thereof (i.e., condensed components of the smoke produced by the combustion of tobacco, leaving flavors and, possibly, nicotine).

Tobacco materials useful in the present disclosure can vary and may include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al., U.S. Pat. No. 4,924,888 to Perfetti et al., U.S. Pat. No. 5,056,537 to Brown et al., U.S. Pat. No. 5,159,942 to Brinkley et al., U.S. Pat. No. 5,220,930 to Gentry, U.S. Pat. No. 5,360,023 to Blakley et al., U.S. Pat. No. 6,701,936 to Shafer et al., U.S. Pat. No. 7,011,096 to Li et al., and U.S. Pat. No. 7,017,585 to Li et al., U.S. Pat. No. 7,025,066 to Lawson et al., U.S. Pat. App. Pub. No. 2004/0255965 to Perfetti et al., PCT Pat. App. Pub. No. WO 02/37990 to Bereman, and Bombick et al., Fund. Appl. Toxicol., 39, p. 11-17 (1997), which are incorporated herein by reference. Further example tobacco compositions that may be useful in a smoking device, including according to the present disclosure, are disclosed in U.S. Pat. No. 7,726,320 to Robinson et al., which is incorporated herein by reference in its entirety.

Still further, the aerosol precursor composition may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the aerosol precursor composition may comprise a blend of flavorful and aromatic tobaccos in cut filler form. In another aspect, the aerosol precursor composition may comprise a reconstituted tobacco material, such as described in U.S. Pat. No. 4,807,809 to Pryor et al., U.S. Pat. No. 4,889,143 to Pryor et al. and U.S. Pat. No. 5,025,814 to Raker, the disclosures of which are incorporated herein by reference in their entirety. For further information regarding suitable aerosol precursor composition, see U.S. patent application Ser. No. 15/916,834 to Sur et al., entitled: Electronically Heated Heat-Not-Burn Smoking Article, filed concurrently herewith, which is incorporated herein by reference.

Regardless of the type of aerosol precursor composition heated, aerosol delivery devices may include a heating element configured to heat the aerosol precursor composition. In some implementations, the heating element is an induction heater. Such heaters often comprise an induction transmitter and an induction receiver. The induction transmitter may include a coil configured to create an oscillating magnetic field (e.g., a magnetic field that varies periodically with time) when alternating current is directed through it. The induction receiver may be at least partially received within the induction transmitter and may include a conductive material. By directing alternating current through the induction transmitter, eddy currents may be generated in the induction receiver via induction. The eddy currents flowing through the resistance of the material defining the induction receiver may heat it by Joule heating (i.e., through the Joule effect). The induction receiver, which may define an atomizer, may be wirelessly heated to form an aerosol from an aerosol precursor composition positioned in proximity to the induction receiver. Various implementations of an aerosol delivery device with an induction heater are described in U.S. Pat. App. Pub. No. 2017/0127722 to Davis et al., U.S. Pat. App. Pub. No. 2017/0202266 to Sur et al., U.S. patent application Ser. No. 15/352,153 to Sur et al., filed Nov. 15, 2016, U.S. patent application Ser. No. 15/799,365 to Sebastian et al., filed Oct. 31, 2017, and U.S. patent application Ser. No. 15/836,086 to Sur, all of which are incorporated by reference herein.

In other implementations including those described more particularly herein, the heating element is a conductive heater such as in the case of electrical resistance heater. These heaters may be configured to produce heat when an electrical current is directed through it. In various implementations, a conductive heater may be provided in a variety of forms, such as in the form of a foil, a foam, discs, spirals, fibers, wires, films, yarns, strips, ribbons or cylinders. Such heaters often include a metal material and are configured to produce heat as a result of the electrical resistance associated with passing an electrical current through it. Such resistive heaters may be positioned in proximity to and heat an aerosol precursor composition to produce an aerosol. A variety of conductive substrates that may be usable with the present disclosure are described in the above-cited U.S. Pat. App. Pub. No. 2013/0255702 to Griffith et al.

In some implementations aerosol delivery devices may include a control body and a cartridge in the case of so-called electronic cigarettes, or a control body and an aerosol source member in the case of heat-not-burn devices. In the case of either electronic cigarettes or heat-not-burn devices, the control body may be reusable, whereas the cartridge/aerosol source member may be configured for a limited number of uses and/or configured to be disposable.

The cartridge/aerosol source member may include the aerosol precursor composition. In order to heat the aerosol precursor composition, the heating element may be positioned in contact with or proximate the aerosol precursor composition, such as across the control body and cartridge, or in the control body in which the aerosol source member may be positioned. The control body may include a power source, which may be rechargeable or replaceable, and thereby the control body may be reused with multiple cartridges/aerosol source members.

The control body may also include means to activate the aerosol delivery device such as a pushbutton, touch-sensitive surface or the like for manual control of the device. Additionally or alternatively, the control body may include a flow sensor to detect when a user draws on the cartridge/aerosol source member to thereby activate the aerosol delivery device.

In various implementations, the aerosol delivery device according to the present disclosure may have a variety of overall shapes, including, but not limited to an overall shape that may be defined as being substantially rod-like or substantially tubular shaped or substantially cylindrically shaped. In the implementations shown in and described with reference to the accompanying figures, the aerosol delivery device has a substantially round cross-section; however, other cross-sectional shapes (e.g., oval, square, triangle, etc.) also are encompassed by the present disclosure. Such language that is descriptive of the physical shape of the article may also be applied to the individual components thereof, including the control body and the cartridge/aerosol source member. In other implementations, the control body may take another handheld shape, such as a small box shape.

In more specific implementations, one or both of the control body and the cartridge/aerosol source member may be referred to as being disposable or as being reusable. For example, the control body may have a power source such as a replaceable battery or a rechargeable battery, solid-state battery, thin-film solid-state battery, rechargeable supercapacitor or the like. One example of a power source is a TKI-1550 rechargeable lithium-ion battery produced by Tadiran Batteries GmbH of Germany. In another implementation, a useful power source may be a N50-AAA CAD-NICA nickel-cadmium cell produced by Sanyo Electric Company, Ltd., of Japan. In other implementations, a plurality of such batteries, for example providing 1.2-volts each, may be connected in series. In some examples, then, the power source may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, or wireless chargers such as those that are radio frequency (RF) based, inductive and the like. Further, in some implementations in the case of an electronic cigarette, the cartridge may comprise a single-use cartridge, as disclosed in U.S. Pat. No. 8,910,639 to Chang et al., which is incorporated herein by reference.

Examples of power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference. With respect to the flow sensor, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. No. 8,881,737 to Collet et al., U.S. Pat. No. 9,423,152 to Ampolini et al., U.S. Pat. No. 9,439,454 to Fernando et al., and U.S. Pat. App. Pub. No. 2015/0257445 to Henry et al., all of which are incorporated herein by reference.

As indicated above, the aerosol delivery device may include at least one control component. A suitable control component may include a number of electronic components, and in some examples may be formed of a printed circuit board (PCB). In some examples, the electronic components include processing circuitry configured to perform data processing, application execution, or other processing, control or management services according to one or more example implementations. The processing circuitry may include a processor embodied in a variety of forms such as at least one processor core, microprocessor, coprocessor, controller, microcontroller or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like.

In some examples, the control component may include one or more input/output peripherals, which may be coupled to or integrated with the processing circuitry. More particularly, the control component may include a communication interface to enable wireless communication with one or more networks, computing devices or other appropriately-enabled devices. Examples of suitable communication interfaces are disclosed in U.S. Pat. App. Pub. No. 2016/0261020 to Marion et al., the content of which is incorporated herein by reference. Another example of a suitable communication interface is the CC3200 single chip wireless microcontroller unit (MCU) from Texas Instruments. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

Still further components can be utilized in the aerosol delivery device of the present disclosure. One example of a suitable component is an indicator such as light-emitting diodes (LEDs), quantum dot-based LEDs or the like, which may be illuminated with use of the aerosol delivery device. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. Pat. No. 9,451,791 to Sears et al., all of which are incorporated herein by reference.

Other indices of operation are also encompassed by the present disclosure. For example, visual indicators of operation also include changes in light color or intensity to show progression of the smoking experience. Tactile (haptic) indicators of operation and sound (audio) indicators of operation similarly are encompassed by the disclosure. Moreover, combinations of such indicators of operation also are suitable to be used in a single smoking article. According to another aspect, the aerosol delivery device may include one or more indicators or indicia, such as, for example, a display configured to provide information corresponding to the operation of the smoking article such as, for example, the amount of power remaining in the power source, progression of the smoking experience, indication corresponding to activating a heat source, and/or the like.

Yet other components are also contemplated. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present article include U.S. Pat. No. 4,735,217 to Gerth et al., U.S. Pat. No. 5,249,586 to Morgan et al., U.S. Pat. No. 5,666,977 to Higgins et al., U.S. Pat. No. 6,053,176 to Adams et al., U.S. Pat. No. 6,164,287 to White, U.S. Pat. No. 6,196,218 to Voges, U.S. Pat. No. 6,810,883 to Felter et al., U.S. Pat. No. 6,854,461 to Nichols, U.S. Pat. No. 7,832,410 to Hon, U.S. Pat. No. 7,513,253 to Kobayashi, U.S. Pat. No. 7,896,006 to Hamano, U.S. Pat. No. 6,772,756 to Shayan, U.S. Pat. Nos. 8,156,944 and 8,375,957 to Hon, U.S. Pat. No. 8,794,231 to Thorens et al., U.S. Pat. No. 8,851,083 to Oglesby et al., U.S. Pat. Nos. 8,915,254 and 8,925,555 to Monsees et al., U.S. Pat. No. 9,220,302 to DePiano et al., U.S. Pat. App. Pub. Nos. 2006/0196518 and 2009/0188490 to Hon, U.S. Pat. App. Pub. No. 2010/0024834 to Oglesby et al., U.S. Pat. App. Pub. No. 2010/0307518 to Wang, PCT Pat. App. Pub. No. WO 2010/091593 to Hon, and PCT Pat. App. Pub. No. WO 2013/089551 to Foo, each of which is incorporated herein by reference. Further, U.S. Pat. App. Pub. No. 2017/0099877 to Worm et al., discloses capsules that may be included in aerosol delivery devices and fob-shape configurations for aerosol delivery devices, and is incorporated herein by reference. A variety of the materials disclosed by the foregoing documents may be incorporated into the present devices in various implementations, and all of the foregoing disclosures are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. No. 8,689,804 to Fernando et al., U.S. Pat. App. Pub. No. 2013/0192623 to Tucker et al., U.S. Pat. No. 9,427,022 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. No. 9,220,302 to DePiano et al., all of which are incorporated herein by reference.

Figure 1:
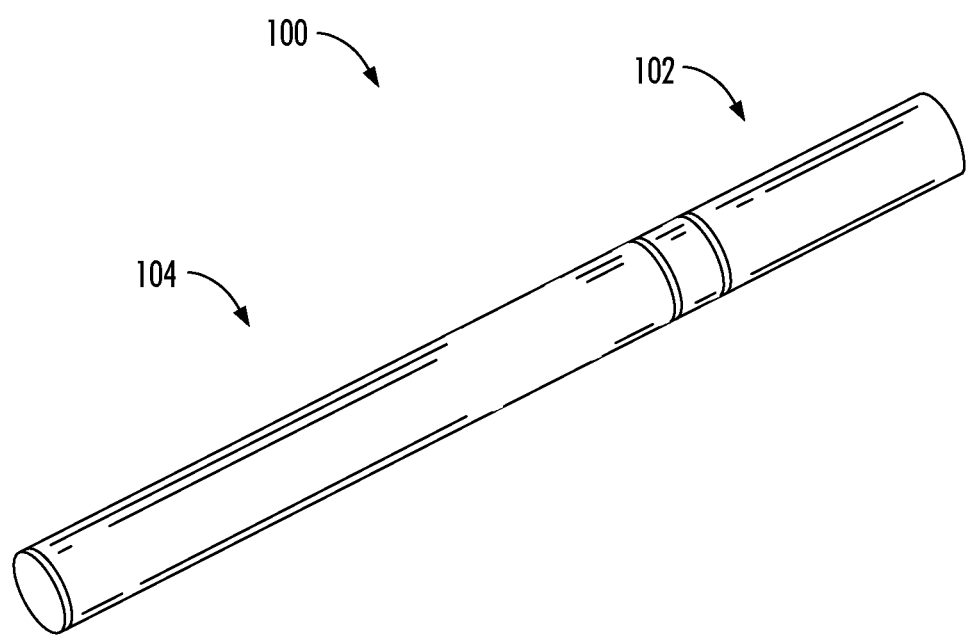
Figure 2:
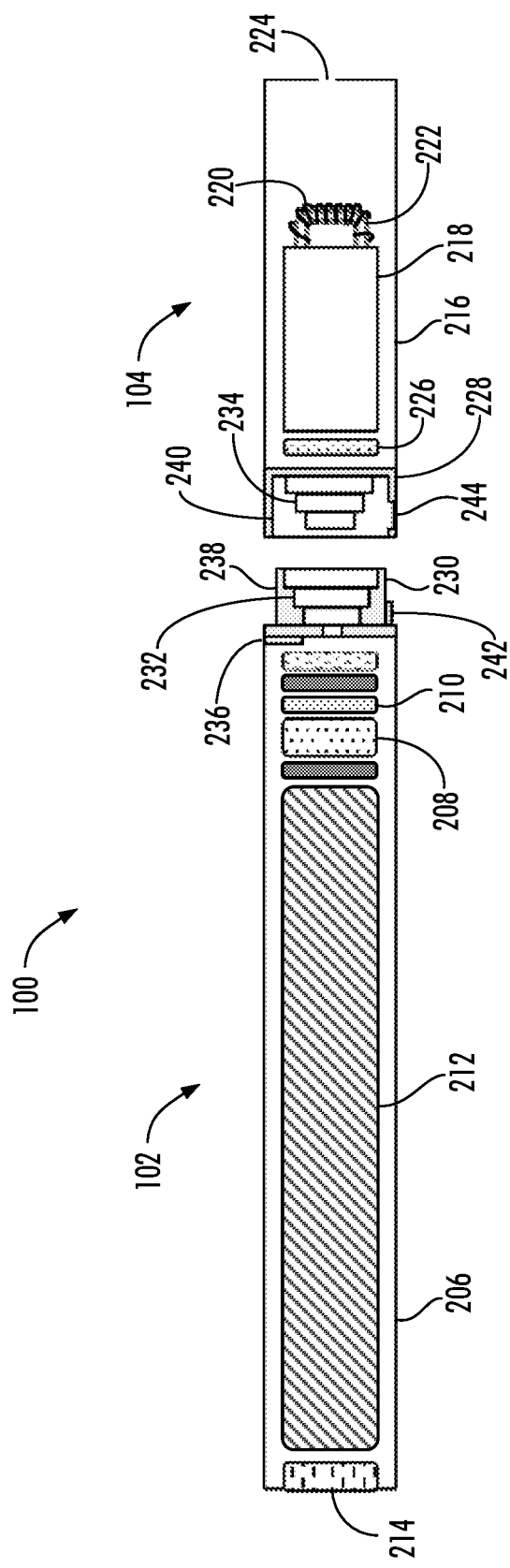
FIG. 2 is a partially cut-away view of the aerosol delivery device of FIG. 1 in which the cartridge and control body are decoupled from one another, according to an example implementation.

FIGS. 1 and 2 illustrate implementations of an aerosol delivery device including a control body and a cartridge in the case of an electronic cigarette. More specifically, FIGS. 1 and 2 illustrate an aerosol delivery device 100 according to an example implementation of the present disclosure. As indicated, the aerosol delivery device may include a control body 102 and a cartridge 104. The control body and the cartridge can be permanently or detachably aligned in a functioning relationship. In this regard, FIG. 1 illustrates a perspective view of the aerosol delivery device in a coupled configuration, whereas FIG. 2 illustrates a partially cut-away side view of the aerosol delivery device in a decoupled configuration. Various mechanisms may connect the cartridge to the control body to result in a threaded engagement, a press-fit engagement, an interference fit, a magnetic engagement, or the like. The aerosol delivery device may be substantially rod-like, substantially tubular shaped, or substantially cylindrically shaped in some implementations when the control body and the cartridge are in an assembled configuration.

As seen in the cut-away view illustrated in FIG. 2, the control body 102 and cartridge 104 each include a number of respective components. The components illustrated in FIG. 2 are representative of the components that may be present in a control body and cartridge and are not intended to limit the scope of components that are encompassed by the present disclosure. As shown, for example, the control body can be formed of a housing 206 (sometimes referred to as a control body shell) that can include a control component 208 (e.g., processing circuitry, etc.), a flow sensor 210, a power source 212 (e.g., a battery, which may be rechargeable, and/or a rechargeable supercapacitor), and an indicator 214 (e.g., LED, quantum dot-based LED), and such components can be variably aligned.

The cartridge 104 can be formed of a housing 216 (sometimes referred to as the cartridge shell) enclosing a reservoir 218 configured to retain the aerosol precursor composition, and including a heating element 220 (sometimes referred to as a heater). In various configurations, this structure may be referred to as a tank; and accordingly, the terms "cartridge," "tank" and the like may be used interchangeably to refer to a shell or other housing enclosing a reservoir for aerosol precursor composition, and including a heating element.

As shown, in some examples, the reservoir 218 may be in fluid communication with a liquid transport element 222 adapted to wick or otherwise transport an aerosol precursor composition stored in the reservoir housing to the heating element 220. In some examples, a valve may be positioned between the reservoir and heating element, and configured to control an amount of aerosol precursor composition passed or delivered from the reservoir to the heating element.

Various examples of materials configured to produce heat when electrical current is applied therethrough may be employed to form the heating element 220. The heating element in these examples may be a resistive heating element such as a wire coil, micro heater or the like. Example materials from which the heating element may be formed include Kanthal (FeCrAl), Nichrome, stainless steel, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heating elements useful in aerosol delivery devices according to the present disclosure are further described below, and can be incorporated into devices such as those described herein.

An opening 224 may be present in the housing 216 (e.g., at the mouth end) to allow for egress of formed aerosol from the cartridge 104.

The cartridge 104 also may include one or more electronic components 226, which may include an integrated circuit, a memory component (e.g., EEPROM, flash memory), a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that various electronic components including the control component and the flow sensor may be combined on a PCB that supports and electrically connects the electronic components. Further, the PCB may be positioned horizontally relative the illustration of FIG. 1 in that the PCB can be lengthwise parallel to the central axis of the control body. In some examples, the air flow sensor may comprise its own PCB or other base element to which it can be attached. In some examples, a flexible PCB may be utilized. A flexible PCB may be configured into a variety of shapes, include substantially tubular shapes. In some examples, a flexible PCB may be combined with, layered onto, or form part or all of a heater substrate.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heating element 220 in the cartridge. Further, the housing 206 can include an air intake 236, which may be a notch in the housing where it connects to the coupler that allows for passage of ambient air around the coupler and into the housing where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the housing 216, in this example. An aerosol precursor composition can be retained in the reservoir. Liquid components, for example, can be sorptively retained by the reservoir. The reservoir can be in fluid connection with the liquid transport element 222. The liquid transport element can transport the aerosol precursor composition stored in the reservoir via capillary action to the heating element 220 that is in the form of a metal wire coil in this example. As such, the heating element is in a heating arrangement with the liquid transport element.

In some examples, a microfluidic chip may be embedded in the reservoir 218, and the amount and/or mass of aerosol precursor composition delivered from the reservoir may be controlled by a micro pump, such as one based on microelectromechanical systems (MEMS) technology. Other example implementations of reservoirs and transport elements useful in aerosol delivery devices according to the present disclosure are further described herein, and such reservoirs and/or transport elements can be incorporated into devices such as those described herein. In particular, specific combinations of heating members and transport elements as further described herein may be incorporated into devices such as those described herein.

In use, when a user draws on the aerosol delivery device 100, airflow is detected by the flow sensor 210, and the heating element 220 is activated to vaporize components of the aerosol precursor composition. Drawing upon the mouth end of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heating element and out the opening 224 in the mouth end of the aerosol delivery device.

FIGS. 3-6 illustrate implementations of an aerosol delivery device including a control body and an aerosol source member in the case of a heat-not-burn device. More specifically, FIG. 3 illustrates an aerosol delivery device 300 according to an example implementation of the present disclosure. The aerosol delivery device may include a control body 302 and an aerosol source member 304. In various implementations, the aerosol source member and the control body can be permanently or detachably aligned in a functioning relationship. In this regard, FIG. 3 illustrates the aerosol delivery device in a coupled configuration, whereas FIG. 4 illustrates the aerosol delivery device in a decoupled configuration. Various mechanisms may connect the aerosol source member to the control body to result in a threaded engagement, a press-fit engagement, an interference fit, a sliding fit, a magnetic engagement, or the like.

As shown in FIG. 4, in various implementations of the present disclosure, the aerosol source member 304 may comprise a heated end 406, which is configured to be inserted into the control body 302, and a mouth end 408, upon which a user draws to create the aerosol. In various implementations, at least a portion of the heated end may include an aerosol precursor composition 410.

In various embodiments, the aerosol source member 304, or a portion thereof, may be wrapped in an overwrap material 412, which may be formed of any material useful for providing additional structure and/or support for the aerosol source member. In various implementations, the overwrap material may comprise a material that resists transfer of heat, which may include a paper or other fibrous material, such as a cellulose material. The overwrap material may also include at least one filler material imbedded or dispersed within the fibrous material. In various implementations, the filler material may have the form of water insoluble particles. Additionally, the filler material can incorporate inorganic components. In various implementations, the overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The overwrap may also include a material typically used in a filter element of a conventional cigarette, such as cellulose acetate. Further, an excess length of the overwrap at the mouth end 408 of the aerosol source member may function to simply separate the aerosol precursor composition 410 from the mouth of a consumer or to provide space for positioning of a filter material, as described below, or to affect draw on the article or to affect flow characteristics of the vapor or aerosol leaving the device during draw. Further discussion relating to the configurations for overwrap materials that may be used with the present disclosure may be found in the above-cited U.S. Pat. No. 9,078,473 to Worm et al.

In various implementations other components may exist between the aerosol precursor composition 410 and the mouth end 408 of the aerosol source member 304, wherein the mouth end may include a filter 414. For example, in some implementations one or any combination of the following may be positioned between the aerosol precursor composition and the mouth end: an air gap; phase change materials for cooling air; flavor releasing media; ion exchange fibers capable of selective chemical adsorption; aerogel particles as filter medium; and other suitable materials.

Various implementations of the present disclosure employ a conductive heater to heat the aerosol precursor composition 410. The conductive heater may comprise an electrical resistance heater in direct contact with, or in proximity to, the aerosol source member and particularly, the aerosol precursor composition of the aerosol source member 304. The electrical resistance heater may be located in the control body and/or the aerosol source member. In some instances, the aerosol precursor composition may include a structure in contact with, or a plurality of beads or particles imbedded in, or otherwise part of, the aerosol precursor composition that may serve as, or facilitate the function of the heater.

FIG. 5 illustrates a front view of an aerosol delivery device 300 according to an example implementation of the present disclosure, and FIG. 6 illustrates a sectional view through the aerosol delivery device of FIG. 5. In particular, the control body 302 of the depicted implementation may comprise a housing 516 that includes an opening 518 defined in an engaging end thereof, a flow sensor 520 (e.g., a puff sensor or pressure switch), a control component 522 (e.g., processing circuitry, etc.), a power source 524 (e.g., a battery, which may be rechargeable, and/or a rechargeable supercapacitor), and an end cap that includes an indicator 526 (e.g., a LED).

In one implementation, the indicator 526 may comprise one or more LEDs, quantum dot-based LEDs or the like. The indicator can be in communication with the control component 522 and be illuminated, for example, when a user draws on the aerosol source member 304, when coupled to the control body 302, as detected by the flow sensor 520.

The control body 302 of the depicted implementation includes one or more heating assemblies 528 (individually or collectively referred to a heating assembly) configured to heat the aerosol precursor composition 410 of the aerosol source member 304. Although the heating assembly of various implementations of the present disclosure may take a variety of forms, in the particular implementation depicted in FIGS. 5 and 6, the heating assembly comprises an outer cylinder 530 and a heating element 532, which in this implementation comprises a plurality of heater prongs that extend from a receiving base 534 (in various configurations, the heating assembly or more specifically the heater prongs may be referred to as a heater). In the depicted implementation, the outer cylinder comprises a double-walled vacuum tube constructed of stainless steel so as to maintain heat generated by the heater prongs within the outer cylinder, and more particularly, maintain heat generated by heater prongs within the aerosol precursor composition. In various implementations, the heater prongs may be constructed of one or more conductive materials, including, but not limited to, copper, aluminum, platinum, gold, silver, iron, steel, brass, bronze, graphite, or any combination thereof.

As illustrated, the heating assembly 528 may extend proximate an engagement end of the housing 516, and may be configured to substantially surround a portion of the heated end 406 of the aerosol source member 304 that includes the aerosol precursor composition 410. In such a manner, the heating assembly may define a generally tubular configuration. As illustrated in FIGS. 5 and 6, the heating element 532 (e.g., plurality of heater prongs) is surrounded by the outer cylinder 530 to create a receiving chamber 536. In such a manner, in various implementations the outer cylinder may comprise a nonconductive insulating material and/or construction including, but not limited to, an insulating polymer (e.g., plastic or cellulose), glass, rubber, ceramic, porcelain, a double-walled vacuum structure, or any combinations thereof.

In some implementations, one or more portions or components of the heating assembly 528 may be combined with, packaged with, and/or integral with (e.g., embedded within) the aerosol precursor composition 410. For example, in some implementations the aerosol precursor composition may be formed of a material as described above and may include one or more conductive materials mixed therein. In some of these implementations, contacts may be connected directly to the aerosol precursor composition such that, when the aerosol source member is inserted into the receiving chamber of the control body, the contacts make electrical connection with the electrical energy source. Alternatively, the contacts may be integral with the electrical energy source and may extend into the receiving chamber such that, when the aerosol source member is inserted into the receiving chamber of the control body, the contacts make electrical connection with the aerosol precursor composition. Because of the presence of the conductive material in the aerosol precursor composition, the application of power from the electrical energy source to the aerosol precursor composition allows electrical current to flow and thus produce heat from the conductive material. Thus, in some implementations the heating element may be described as being integral with the aerosol precursor composition. As a non-limiting example, graphite or other suitable, conductive material may be mixed with, embedded in, or otherwise present directly on or within the material forming the aerosol precursor composition to make the heating element integral with the medium.

As noted above, in the illustrated implementation, the outer cylinder 530 may also serve to facilitate proper positioning of the aerosol source member 304 when the aerosol source member is inserted into the housing 516. In various implementations, the outer cylinder of the heating assembly 528 may engage an internal surface of the housing to provide for alignment of the heating assembly with respect to the housing. Thereby, as a result of the fixed coupling between the heating assembly, a longitudinal axis of the heating assembly may extend substantially parallel to a longitudinal axis of the housing. In particular, the support cylinder may extend from the opening 518 of the housing to the receiving base 534 to create the receiving chamber 536.

The heated end 406 of the aerosol source member 304 is sized and shaped for insertion into the control body 302. In various implementations, the receiving chamber 536 of the control body may be characterized as being defined by a wall with an inner surface and an outer surface, the inner surface defining the interior volume of the receiving chamber. For example, in the depicted implementations, the outer cylinder 530 defines an inner surface defining the interior volume of the receiving chamber. In the illustrated implementation, an inner diameter of the outer cylinder may be slightly larger than or approximately equal to an outer diameter of a corresponding aerosol source member (e.g., to create a sliding fit) such that the outer cylinder is configured to guide the aerosol source member into the proper position (e.g., lateral position) with respect to the control body. Thus, the largest outer diameter (or other dimension depending upon the specific cross-sectional shape of the implementations) of the aerosol source member may be sized to be less than the inner diameter (or other dimension) at the inner surface of the wall of the open end of the receiving chamber in the control body. In some implementations, the difference in the respective diameters may be sufficiently small so that the aerosol source member fits snugly into the receiving chamber, and frictional forces prevent the aerosol source member from being moved without an applied force. On the other hand, the difference may be sufficient to allow the aerosol source member to slide into or out of the receiving chamber without requiring undue force.

In the illustrated implementation, the control body 302 is configured such that when the aerosol source member 304 is inserted into the control body, the heating element 532 (e.g., heater prongs) is located in the approximate radial center of at least a portion of the aerosol precursor composition 410 of the heated end 406 of the aerosol source member. In such a manner, when used in conjunction with a solid or semi-solid aerosol precursor composition, the heater prongs may be in direct contact with the aerosol precursor composition. In other implementations, such as when used in conjunction with an extruded aerosol precursor composition that defines a tube structure, the heater prongs may be located inside of a cavity defined by an inner surface of the extruded tube structure, and would not contact the inner surface of the extruded tube structure.

During use, the consumer initiates heating of the heating assembly 528, and in particular, the heating element 532 that is adjacent the aerosol precursor composition 410 (or a specific layer thereof). Heating of the aerosol precursor composition releases the inhalable substance within the aerosol source member 304 so as to yield the inhalable substance. When the consumer inhales on the mouth end 408 of the aerosol source member, air is drawn into the aerosol source member through an air intake 538 such as openings or apertures in the control body 302. The combination of the drawn air and the released inhalable substance is inhaled by the consumer as the drawn materials exit the mouth end of the aerosol source member. In some implementations, to initiate heating, the consumer may manually actuate a pushbutton or similar component that causes the heating element of the heating assembly to receive electrical energy from the battery or other energy source. The electrical energy may be supplied for a pre-determined length of time or may be manually controlled.

In some implementations, flow of electrical energy does not substantially proceed in between puffs on the device 300 (although energy flow may proceed to maintain a baseline temperature greater than ambient temperature—e.g., a temperature that facilitates rapid heating to the active heating temperature). In the depicted implementation, however, heating is initiated by the puffing action of the consumer through use of one or more sensors, such as flow sensor 520. Once the puff is discontinued, heating will stop or be reduced. When the consumer has taken a sufficient number of puffs so as to have released a sufficient amount of the inhalable substance (e.g., an amount sufficient to equate to a typical smoking experience), the aerosol source member 304 may be removed from the control body 302 and discarded. In some implementations, further sensing elements, such as capacitive sensing elements and other sensors, may be used as discussed in U.S. patent application Ser. No. 15/707,461 to Phillips et al., which is incorporated herein by reference in its entirety.

In various implementations, the aerosol source member 304 may be formed of any material suitable for forming and maintaining an appropriate conformation, such as a tubular shape, and for retaining therein the aerosol precursor composition 410. In some implementations, the aerosol source member may be formed of a single wall or, in other implementations, multiple walls, and may be formed of a material (natural or synthetic) that is heat resistant so as to retain its structural integrity—e.g., does not degrade—at least at a temperature that is the heating temperature provided by the electrical heating element, as further discussed herein. While in some implementations, a heat resistant polymer may be used, in other implementations, the aerosol source member may be formed from paper, such as a paper that is substantially straw-shaped. As further discussed herein, the aerosol source member may have one or more layers associated therewith that function to substantially prevent movement of vapor therethrough. In one example implementation, an aluminum foil layer may be laminated to one surface of the aerosol source member. Ceramic materials also may be used. In further implementations, an insulating material may be used so as not to unnecessarily move heat away from the aerosol precursor composition. Further example types of components and materials that may be used to provide the functions described above or be used as alternatives to the materials and components noted above can be those of the types set forth in U.S. Pat. App. Pub. Nos. 2010/00186757 to Crooks et al., 2010/00186757 to Crooks et al., and 2011/0041861 to Sebastian et al., all of which are incorporated herein by reference.

In the depicted implementation, the control body 302 includes a control component 522 that controls the various functions of the aerosol delivery device 300, including providing power to the electrical heating element 532. For example, the control component may include processing circuitry (which may be connected to further components, as further described herein) that is connected by electrically conductive wires (not shown) to the power source 524. In various implementations, the processing circuitry may control when and how the heating assembly 528, and particularly the heater prongs, receives electrical energy to heat the aerosol precursor composition 410 for release of the inhalable substance for inhalation by a consumer. In some implementations, such control may be activated by a flow sensor 520 as described in greater detail above.

As seen in FIGS. 5 and 6, the heating assembly 528 of the depicted implementation comprises an outer cylinder 530 and a heating element 532 (e.g., plurality of heater prongs) that extend from a receiving base 534. In some implementations, such as those wherein the aerosol precursor composition 410 comprises a tube structure, the heater prongs may be configured to extend into a cavity defined by the inner surface of the aerosol precursor composition. In other implementations, such as the depicted implementation wherein the aerosol precursor composition comprises a solid or semi-solid, the plurality of heater prongs are configured to penetrate into the aerosol precursor composition contained in the heated end 406 of the aerosol source member 304 when the aerosol source member is inserted into the control body 302. In such implementations, one or more of the components of the heating assembly, including the heater prongs and/or the receiving base, may be constructed of a non-stick or stick-resistant material, for example, certain aluminum, copper, stainless steel, carbon steel, and ceramic materials. In other implementations, one or more of the components of the heating assembly, including the heater prongs and/or the receiving base, may include a non-stick coating, including, for example, a polytetrafluoroethylene (PTFE) coating, such as Teflon®, or other coatings, such as a stick-resistant enamel coating, or a ceramic coating, such as Greblon®, or Thermolon™, or a ceramic coating, such as Greblon®, or Thermolon™.

In addition, although in the depicted implementation there are multiple heater prongs 532 that are substantially equally distributed about the receiving base 534, it should be noted that in other implementations, any number of heater prongs may be used, including as few as one, with any other suitable spatial configuration. Furthermore, in various implementations the length of the heater prongs may vary. For example, in some implementations the heater prongs may comprise small projections, while in other implementations the heater prongs may extend any portion of the length of the receiving chamber 536, including up to about 25%, up to about 50%, up to about 75%, and up to about the full length of the receiving chamber. In still other implementations, the heating assembly 528 may take on other configurations. Examples of other heater configurations that may be adapted for use in the present invention per the discussion provided above can be found in U.S. Pat. No. 5,060,671 to Counts et al., U.S. Pat. No. 5,093,894 to Deevi et al., U.S. Pat. No. 5,224,498 to Deevi et al., U.S. Pat. No. 5,228,460 to Sprinkel Jr., et al., U.S. Pat. No. 5,322,075 to Deevi et al., U.S. Pat. No. 5,353,813 to Deevi et al., U.S. Pat. No. 5,468,936 to Deevi et al., U.S. Pat. No. 5,498,850 to Das, U.S. Pat. No. 5,659,656 to Das, U.S. Pat. No. 5,498,855 to Deevi et al., U.S. Pat. No. 5,530,225 to Hajaligol, U.S. Pat. No. 5,665,262 to Hajaligol, U.S. Pat. No. 5,573,692 to Das et al.; and U.S. Pat. No. 5,591,368 to Fleischhauer et al., which are incorporated herein by reference in their entireties.

In various implementations, the control body 302 may include an air intake 538 (e.g., one or more openings or apertures) therein for allowing entrance of ambient air into the interior of the receiving chamber 536. In such a manner, in some implementations the receiving base 534 may also include an air intake. Thus, in some implementations when a consumer draws on the mouth end of the aerosol source member 304, air can be drawn through the air intake of the control body and the receiving base into the receiving chamber, pass into the aerosol source member, and be drawn through the aerosol precursor composition 410 of the aerosol source member for inhalation by the consumer. In some implementations, the drawn air carries the inhalable substance through the optional filter 414 and out of an opening at the mouth end 408 of the aerosol source member. With the heating element 532 positioned inside the aerosol precursor composition, the heater prongs may be activated to heat the aerosol precursor composition and cause release of the inhalable substance through the aerosol source member.

Other implementations of the aerosol delivery device, control body and aerosol source member are described in the above-cited U.S. patent application Ser. No. 15/916,834 to Sur et al., entitled: Electronically Heated Heat-Not-Burn Smoking Article, filed concurrently herewith, which is again incorporated herein by reference.

Figure 7A:
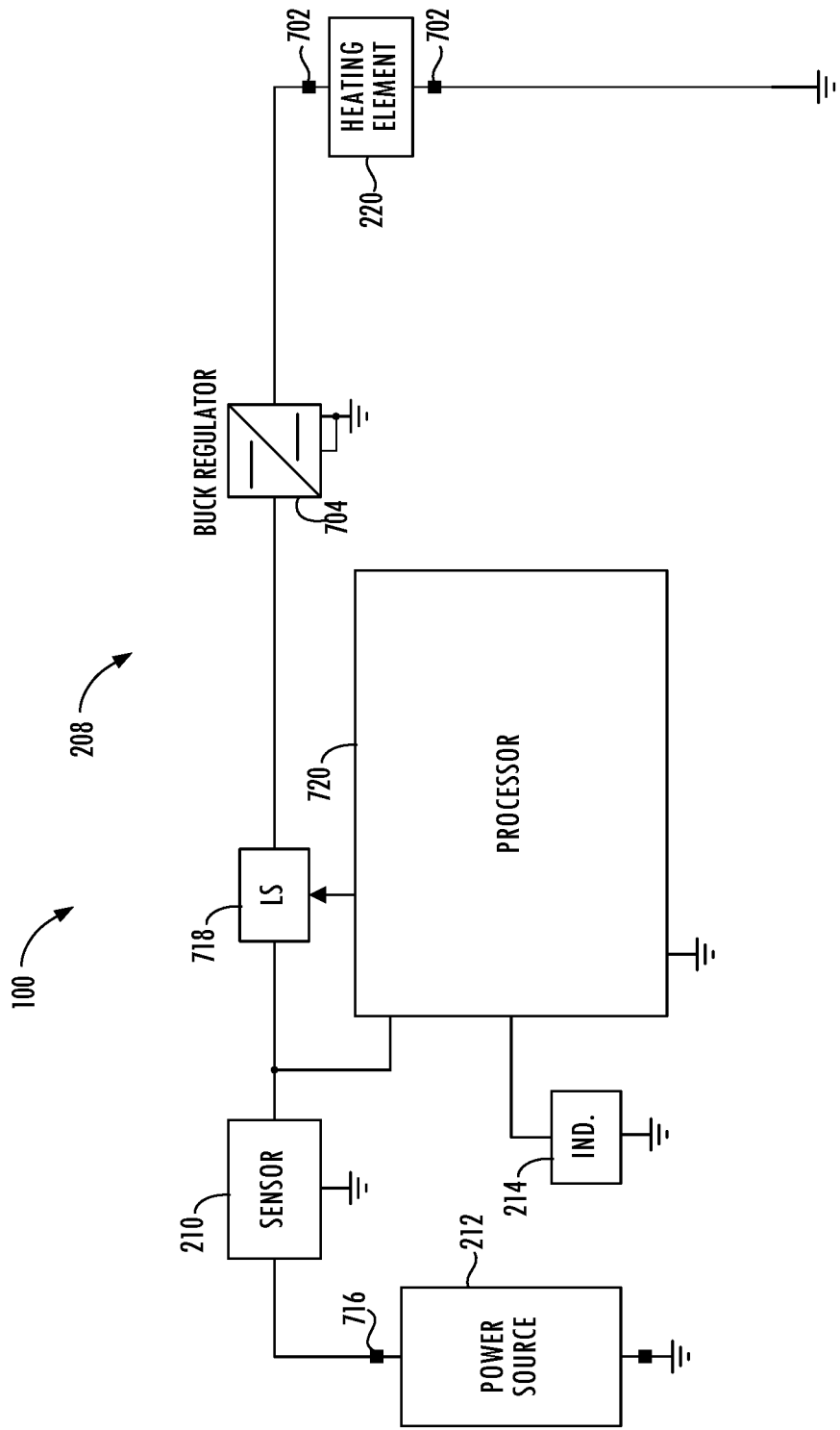
Figure 7B:
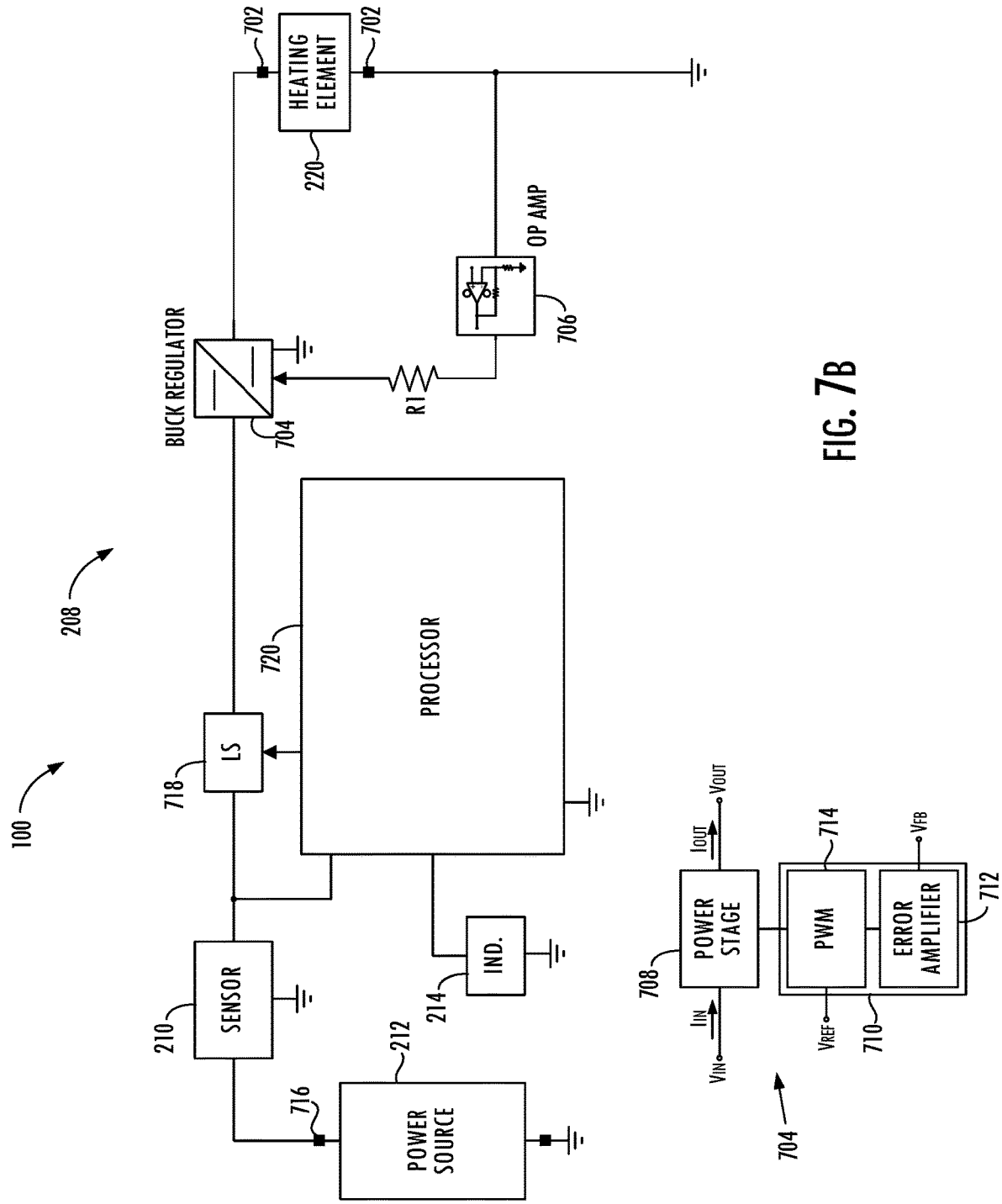
Figure 8:
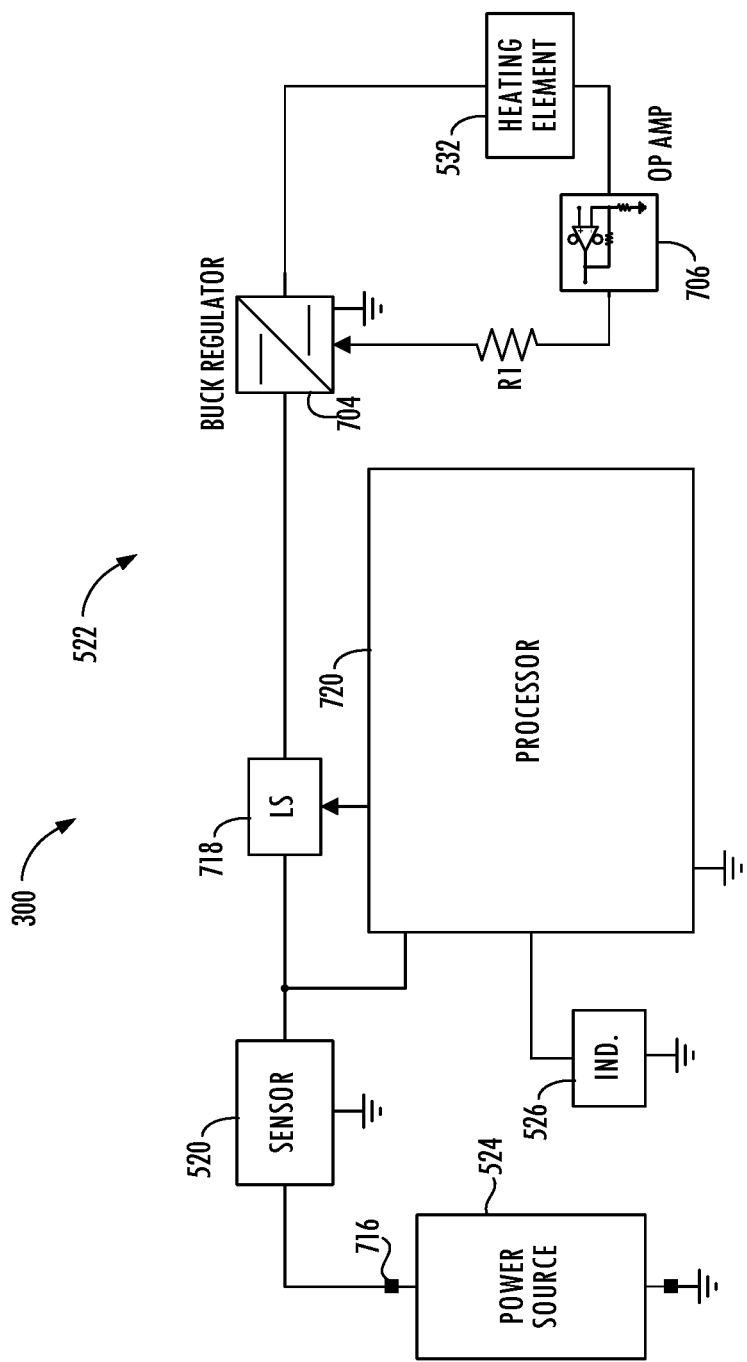

As described above, the aerosol delivery device of example implementations may include circuitry in the context of either an electronic cigarette or a heat-not-burn device, or even in the case of a device that includes the functionality of both. FIGS. 7A, 7B, 8 and 9 are circuit diagrams of aerosol delivery devices according to various example implementations of the present disclosure. More particularly, FIGS. 7A and 7B are circuit diagrams of the aerosol delivery device 100 shown and described above in the context of an electronic cigarette. FIG. 8 is a circuit diagram of the aerosol delivery device 300 shown and described above in the context of a heat-not-burn device, according to some example implementations of the present disclosure.

As shown in FIGS. 7A and 7B, the aerosol delivery device 100 includes a control component 208, flow sensor 210, power source 212, indicator 214 and heating element 220; and in particular examples in which the heating element is part of a cartridge 102, the aerosol delivery device (or more specifically its control body 104) may include terminals 702 coupled or coupleable to the heating element. Similarly, as shown in FIG. 8, the aerosol delivery device 300 includes a control component 522, flow sensor 520, power source 524, indicator 526 and heating element 532.

As described above in the case of either aerosol delivery device 100 or aerosol delivery device 300, the control component 208, 522 is coupled to and configured to controllably power the heating element 220, 532 that is configured to convert electricity to heat and thereby vaporize components of aerosol precursor composition. As shown, the control component includes a buck regulator circuit 704 coupled to the heating element, and configured to step down voltage and step up current from the power source to the heating element to thereby power the heating element. The buck regulator circuit may or may not include a feedback feature. One example of a suitable buck regulator circuit includes the model ADP2165 or model ADP2166 DC-to-DC regulator from Analog Devices, which does include a feedback feature. For a buck regulator circuit with feedback, the feedback may be grounded as shown in FIG. 7A.

As shown in FIGS. 7B and 8, in other examples in which the buck regulator circuit 704 has a feedback feature, the control component 208, 522 includes an operational amplifier circuit 706 coupled to the heating element 220, 532 and buck regulator circuit. The operational amplifier circuit in these examples may be configured to amplify an output voltage from the heating element to produce a higher voltage that is fed back to the buck regulator circuit In some examples such as those shown, the operational amplifier circuit is a non-inverting operational amplifier circuit.

As also shown in FIG. 7B, the buck regulator circuit 704 may include a power stage 708 configured to step down the voltage and step up the current from the power source 212, 524, and a feedback control circuit 710 configured to use the higher voltage from the operational amplifier circuit 706 to regulate an output voltage from the buck regulator circuit to the heating element 220, 532. The feedback control circuit may further include an error amplifier 712 and a pulse width modulation (PWM) comparator 714. The error amplifier may be configured to produce a control voltage based on a comparison of the higher voltage and a reference voltage, And the PWM comparator may be configured to use the control voltage to produce a PWM waveform that is used to regulate the output voltage from the buck regulator circuit to the heating element.

In some examples, the aerosol delivery device 100, 300 has terminals including a positive terminal 716 to which the power source 212, 524 is connected or connectable. The control component 208, 522 may further include a high-side load switch (LS) 718 between the buck regulator circuit 704 and the positive terminal, with the high-side load switch being configured to connect and disconnect the power source to and from a load including the heating element 220, 532, and limit input current to the buck regulator circuit. This also acts as a protection circuit just in case the current spikes above a threshold safety factor. That is, the high-side load switch also acts as a safety feature in that it ensures that the input current doesn't go above the threshold safety factor.

Even further, the flow sensor 210, 520 may be between the positive terminal 716 and the high-side load switch 718. The sensor may be configured to produce a measurement of pressure caused by airflow through at least a portion of the aerosol delivery device 100, 300, and convert the measurement of pressure to a corresponding electrical signal. A processor 720 of the control component 208, 522 may be configured to receive the corresponding electrical signal and control the high-side load switch to connect the power source 212, 524 to the load in response thereto.

In some examples, the aerosol delivery device 100, 300 further includes a resistor R1 coupled in series between the operational amplifier circuit 706 and the buck regulator circuit 704. In these examples, the resistor may be configured to limit current fed back to the buck regulator circuit from the operational amplifier circuit.

Figure 9:
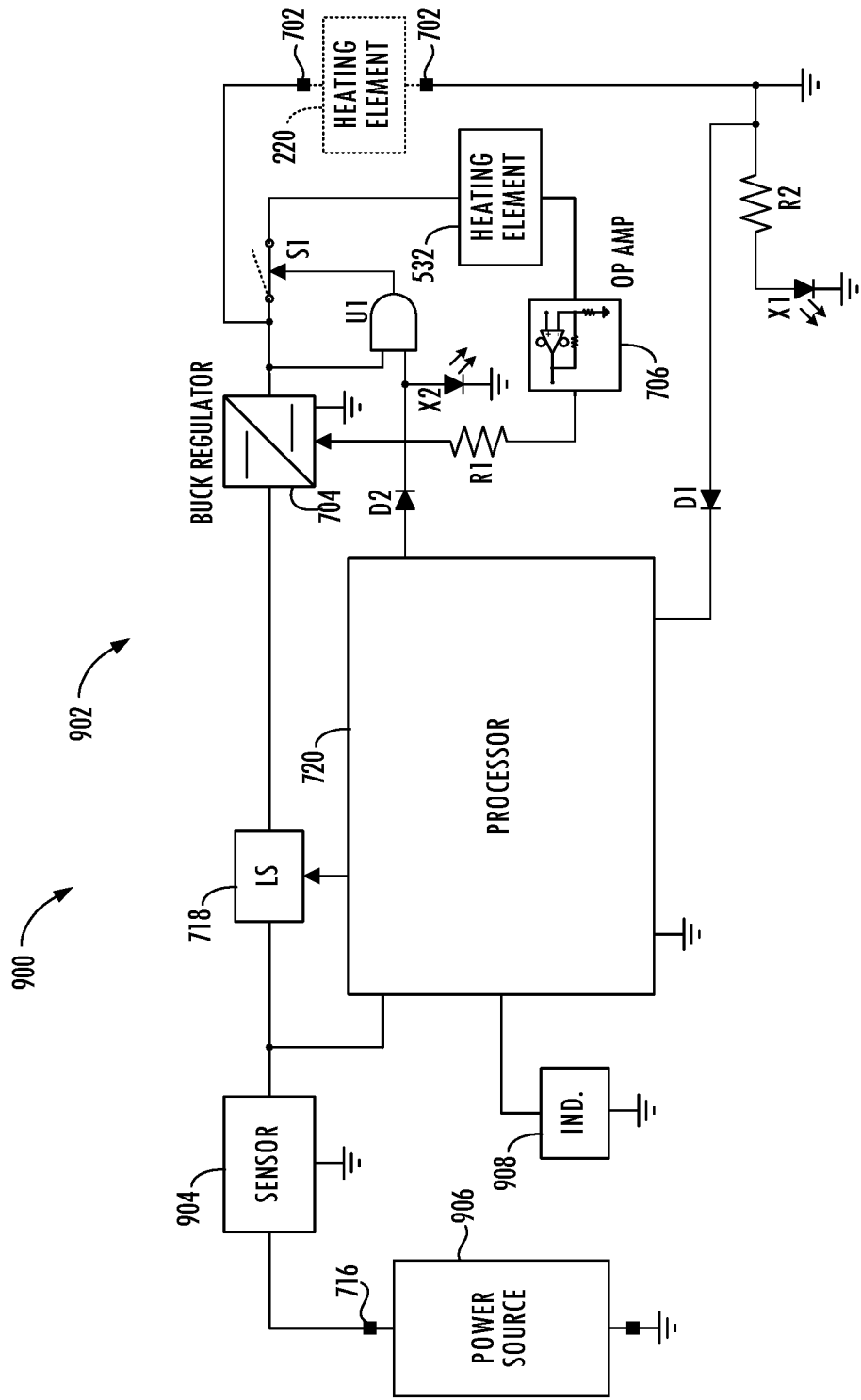

FIG. 9 is a circuit diagram of an aerosol delivery device 900 that incorporates the functionality of both an electronic cigarette and heat-not-burn device. As shown, the aerosol delivery device includes a control component 902, flow sensor 904, power source 906 and indicator 908, which may correspond to or include the functionality of respective ones of the control component 208, 522, flow sensor 210, 520, power source 212, 524 and indicator 214, 526. The aerosol delivery device may include a (first) heating element 532 (first heating element), and a (second) heating element 220 that may be detachably coupled to the aerosol delivery device via terminals 702.

Similar to the implementations in FIGS. 7B and 8, the control component 902 may include a buck regulator circuit 704 and operational amplifier circuit 706. The control component may also include a high-side load switch 718 between the buck regulator circuit and positive terminal 716 to the power source 906, and a processor 720. The flow sensor 904 may be between the positive terminal and high-side load switch. The aerosol delivery device may also include a resistor R1 between the operational amplifier circuit and the buck regulator circuit, as described above.

In the implementation shown in FIG. 9, the first heating element 532 is configured to vaporize components of a (first) aerosol precursor composition that is a solid or semi-solid. The second heating element 220 is configured to vaporize components of a (second) aerosol precursor composition that is a liquid. The control component 902 further includes a switch Si coupled to an output of the buck regulator circuit 704 and switchable to provide an output voltage and current from the buck regulator circuit to the first heating element or the second heating element. More specifically, for example, the switch may be switchable to provide the output voltage and current from the buck regulator circuit to the first heating element when the second heating element is not coupled to the terminals, and to the second heating element when the second heating element is coupled to the terminals.

The processor 720 may be configured to determine when the second heating element 220 is coupled to the terminals 702. In some examples, the processor includes an input at which the processor is coupled to the terminal, (or one of the terminals such as the negative terminal), such as with a series diode D1. In this manner, the second heating element being coupled to the terminals causes a logical high level of voltage at the input of the processor, which the processor may interpret and thereby determine that the second heating element is coupled to the terminals.

As also shown, the control component 902 may further include one or more logic gates U1 with first and second inputs, and an output. The first input is coupled to the output of the buck regulator circuit 704 between the buck regulator circuit and the switch S1. The second input is coupled to the processor 720 (between which the control component may include a diode D2). The output is coupled to the switch.

In examples including the one or more logic gates U1, the output voltage from the buck regulator circuit 704 causes a logical high level of voltage at the first input of the one or more logic gates. The processor 720 is configured to cause a first logical level of voltage at the second input of the one or more logic gates when the second heating element 220 is not coupled to the terminals 702 to cause a logical low level of voltage at the output of the one or more logic gates, which is in turn configured to control the switch S1 to provide the output voltage and current to the first heating element 532. Conversely, the processor is configured to cause an opposite, second logical level of voltage at the second input of the one or more logic gates when the second heating element is coupled to the terminals to cause a logical high level of voltage at the output of the one or more logic gates, which is in turn configured to control the switch to provide the output voltage and current to the second heating element.

As shown, in some examples, the one or more logic gates U1 are or include an AND gate or other logic gates that may be configured or arranged to implement a logical conjunction. In other configurations, an AND gate may be made from NAND gates, NOR gates, or the like. In these examples, the first logical level of voltage caused by the processor 720 may be a logical low level of voltage at the second input of the AND gate or other similarly configured logic gate(s), and the second logical level of voltage caused by the processor may be a logical high level of voltage. In other configurations of the logic gate(s), the first and opposite, second logic levels may be respectively logical high and low levels of voltage at the second input of the logic gate(s).

As also shown, the aerosol delivery device 900 may be configured to provide user-perceptible feedback to indicate which of the first heating element 532 or second heating element 220 is enabled to vaporize solid, semi-solid or liquid aerosol precursor composition. This may be provided by respective indicators such as LEDs X1 and X2. As shown, LED X1 may be coupled between the processor 720 and the second input of the one or more logic gates U1. The other, LED X2 may be coupled between the processor and the terminals 702, or more specifically for example, the one of the terminals (e.g., negative terminal) to which the processor is coupled. A second resistor R2 may be coupled between the one of the terminals and LED X2.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. An aerosol delivery device comprising:
    a housing structured to retain an aerosol precursor composition;
    a heating element configured to convert electricity to heat and thereby vaporize components of the aerosol precursor composition;
    a positive terminal to which a power source is connected or connectable;
    a control component coupled to and configured to controllably power the heating element, the control component including:
        a buck regulator circuit coupled to the heating element, and configured to step down voltage and step up current from the power source to the heating element to thereby power the heating element;
        an operational amplifier circuit coupled to the heating element and buck regulator circuit, and configured to amplify an output voltage from the heating element to produce a higher voltage that is fed back to the buck regulator circuit; and
        a high-side load switch between the buck regulator circuit and the positive terminal, the high-side load switch configured to connect and disconnect the power source to and from a load including the heating element, and limit input current to the buck regulator circuit; and
        a sensor between the positive terminal and the high-side load switch, the sensor configured to produce a measurement of pressure caused by airflow through at least a portion of the aerosol delivery device, and convert the measurement of pressure to a corresponding electrical signal,
    wherein the control component further includes a processor configured to receive the corresponding electrical signal and control the high-side load switch to connect the power source to the load in response thereto, and
    wherein the buck regulator circuit includes a power stage configured to step down the voltage and step up the current from the power source, and a feedback control circuit configured to use the higher voltage from the operational amplifier circuit to regulate an output voltage from the buck regulator circuit to the heating element.

2. The aerosol delivery device of claim 1, wherein the feedback control circuit includes an error amplifier and a pulse width modulation (PWM) comparator, the error amplifier being configured to produce a control voltage based on a comparison of the higher voltage and a reference voltage, and the PWM comparator being configured to use the control voltage to produce a PWM waveform that is used to regulate the output voltage from the buck regulator circuit to the heating element.

3. The aerosol delivery device of claim 1, wherein the operational amplifier circuit is a non-inverting operational amplifier circuit.

4. The aerosol delivery device of claim 1 further comprising a resistor coupled in series between the operational amplifier circuit and the buck regulator circuit, the resistor being configured to limit current fed back to the buck regulator circuit from the operational amplifier circuit.

5. The aerosol delivery device of claim 1, wherein the aerosol precursor composition is a liquid, or a solid or semi-solid.

6. The aerosol delivery device of claim 1, wherein the aerosol precursor composition is a first aerosol precursor composition that is a solid or semi-solid, the heating element is a first heating element configured to vaporize components of the first aerosol precursor composition, and the aerosol delivery device further comprises:
    terminals coupled or coupleable to a second heating element of a cartridge configured to retain a second aerosol precursor composition that is a liquid, and the second heating element being configured to convert electricity to heat and thereby vaporize components of the second aerosol precursor composition, and
    wherein the control component further includes a switch coupled to an output of the buck regulator circuit and switchable to provide an output voltage and current from the buck regulator circuit to the first heating element or the second heating element.

7. The aerosol delivery device of claim 6, wherein the switch is switchable to provide the output voltage and current from the buck regulator circuit to the first heating element when the second heating element is not coupled to the terminals, and to the second heating element when the second heating element is coupled to the terminals.

8. The aerosol delivery device of claim 7, wherein the control component further includes:
    one or more logic gates with a first input coupled to the output of the buck regulator circuit between the buck regulator circuit and the switch, a second input coupled to the processor, and an output coupled to the switch, wherein the output voltage from the buck regulator circuit causes a logical high level of voltage at the first input of the one or more logic gates, and
    wherein the processor is configured to determine when the second heating element is coupled to the terminals, and to cause a first logical level of voltage at the second input of the one or more logic gates when the second heating element is not coupled to the terminals to cause a logical low level of voltage at the output of the one or more logic gates that is configured to control the switch to provide the output voltage and current to the first heating element, and the processor is configured to cause an opposite, second logical level of voltage at the second input of the one or more logic gates when the second heating element is coupled to the terminals to cause a logical high level of voltage at the output of the one or more logic gates that is configured to control the switch to provide the output voltage and current to the second heating element.

9. A control body for an aerosol delivery device, the control body comprising:
 a positive terminal to which a power source is connected or connectable;
 a control component coupled to and configured to controllably power a heating element configured to convert electricity to heat and thereby vaporize components of an aerosol precursor composition, the control component including:
  a buck regulator circuit coupled to the heating element, and configured to step down voltage and step up current from the power source to the heating element to thereby power the heating element;
  an operational amplifier circuit coupled to the heating element and buck regulator circuit, and configured to amplify an output voltage from the heating element to produce a higher voltage that is fed back to the buck regulator circuit; and
  a high-side load switch between the buck regulator circuit and the positive terminal, the high-side load switch configured to connect and disconnect the power source to and from a load including the heating element, and limit input current to the buck regulator circuit; and
 a sensor between the positive terminal and the high-side load switch, the sensor configured to produce a measurement of pressure caused by airflow through at least a portion of the aerosol delivery device, and convert the measurement of pressure to a corresponding electrical signal,
 wherein the control component further includes a processor configured to receive the corresponding electrical signal and control the high-side load switch to connect the power source to the load in response thereto, and
 wherein the buck regulator circuit includes a power stage configured to step down the voltage and step up the current from the power source, and a feedback control circuit configured to use the higher voltage from the operational amplifier circuit to regulate an output voltage from the buck regulator circuit to the heating element.

10. The control body of claim 9, wherein the feedback control circuit includes an error amplifier and a pulse width modulation (PWM) comparator, the error amplifier being configured to produce a control voltage based on a comparison of the higher voltage and a reference voltage, and the PWM comparator being configured to use the control voltage to produce a PWM waveform that is used to regulate the output voltage from the buck regulator circuit to the heating element.

11. The control body of claim 9, wherein the operational amplifier circuit is a non-inverting operational amplifier circuit.

12. The control body of claim 9 further comprising a resistor coupled in series between the operational amplifier circuit and the buck regulator circuit, the resistor being configured to limit current fed back to the buck regulator circuit from the operational amplifier circuit.

13. The control body of claim 9, wherein the aerosol precursor composition is a liquid, or a solid or semi-solid.

14. The control body of claim 9, wherein the control body includes the heating element that is a first heating element configured to vaporize components of a first aerosol precursor composition that is a solid or semi-solid, and terminals coupleable to a second heating element configured to convert electricity to heat and thereby vaporize components of a second aerosol precursor composition that is a liquid, and
 wherein the control component further includes a switch coupled to an output of the buck regulator circuit and switchable to provide an output voltage and current from the buck regulator circuit to the first heating element or the second heating element.

15. The control body of claim 14, wherein the switch is switchable to provide the output voltage and current from the buck regulator circuit to the first heating element when the second heating element is not coupled to the terminals, and to the second heating element when the second heating element is coupled to the terminals.

16. The control body of claim 15, wherein the control component further includes:
 one or more logic gates with a first input coupled to the output of the buck regulator circuit between the buck regulator circuit and the switch, a second input coupled to the processor, and an output coupled to the switch, wherein the output voltage from the buck regulator circuit causes a logical high level of voltage at the first input of the one or more logic gates, and
 wherein the processor is configured to determine when the second heating element is coupled to the terminals, and to cause a first logical level of voltage at the second input of the one or more logic gates when the second heating element is not coupled to the terminals to cause a logical low level of voltage at the output of the one or more logic gates that is configured to control the switch to provide the output voltage and current to the first heating element, and the processor is configured to cause an opposite, second logical level of voltage at the second input of the one or more logic gates when the second heating element is coupled to the terminals to cause a logical high level of voltage at the output of the one or more logic gates that is configured to control the switch to provide the output voltage and current to the second heating element.

\* \* \* \* \*